United States Patent [19]

Rao et al.

[11] Patent Number: 5,278,074
[45] Date of Patent: Jan. 11, 1994

[54] METHOD OF MONITORING AND CONTROLLING CORROSION INHIBITOR DOSAGE IN AQUEOUS SYSTEMS

[75] Inventors: Narasimha M. Rao, Aurora; Frank F.-Y. Lu, Naperville; John E. Hoots, St. Charles, all of Ill.

[73] Assignee: Nalco Chemical Company, Naperville, Ill.

[21] Appl. No.: 872,624

[22] Filed: Apr. 22, 1992

[51] Int. Cl.⁵ .............................................. G01N 21/64
[52] U.S. Cl. ........................................ 436/52; 436/92; 436/98; 436/163; 436/172; 436/174; 436/815
[58] Field of Search ............... 436/52, 56, 91, 92, 436/96, 98, 106, 163, 172, 174, 175, 800, 815; 422/62

[56] References Cited

U.S. PATENT DOCUMENTS 4,783,314  11/1988  Hoots et al. ........................ 422/3
4,992,380  2/1991   Moriarty et al. ..................... 436/55
5,041,386  8/1991   Pierce et al. ........................ 436/50
5,120,661  6/1992   Baker et al. ........................ 436/164
5,128,419  7/1992   Fong et al. .......................... 525/351

FOREIGN PATENT DOCUMENTS 0062306  10/1982  European Pat. Off.
2238383   5/1991  United Kingdom.

*Primary Examiner*—James C. Housel
*Assistant Examiner*—Jeffrey R. Snay
*Attorney, Agent, or Firm*—Joan I. Norek; Robert A. Miller; Joseph B. Barrett

[57] ABSTRACT

The concentration of an aromatic azole corrosion inhibitor in the water of an aqueous system is monitored by a fluorometric method which is based upon the measurement of the fluorescence intensity of the aromatic azole corrosion inhibitor itself, and the precise determination of concentration permits control of the dosage of such aromatic azole corrosion inhibitor.

22 Claims, 5 Drawing Sheets

PRIOR ART PROCEDURE

METHOD OF MONITORING AND CONTROLLING CORROSION INHIBITOR DOSAGE IN AQUEOUS SYSTEMS

TECHNICAL FIELD OF THE INVENTION

The present invention is in the technical field of monitoring and controlling the dosage of corrosion inhibitors in aqueous systems.

BACKGROUND OF THE INVENTION

Corrosion of processed metals, such as steel, copper, and zinc, is a process whereby elemental metals, in the presence of water and oxygen, are converted to oxides. Although corrosion is a complicated process, it may be considered an electrochemical reaction involving three steps which occur at the anodic and cathodic sites of a metal surface, as follows:

1. Loss of metal to the water solution in oxidized cationic form at an anodic site, with concomitant release of electrons ("anodic reaction");
2. The flow of the released electrons to a cathodic site; and
3. Oxygen at a cathodic site uses the electrons to form hydroxyl ions ("cathodic" reaction), which flow to an anodic site.

These three basic steps are necessary for corrosion to proceed, and the slowest of the three steps determines the rate of the overall corrosion process. The cathodic reaction is often the slowest of the three steps because the diffusion rate of oxygen through water is slow.

A corrosion control program usually depends on specific inhibitors to minimize the anodic or cathodic reaction, or both. Among the various types of corrosion inhibitors are organic compounds, which act by adsorbing or chemisorbing as thin layers on metal surfaces to separate the water and metal. These materials form and maintain a dynamic barrier between the water and metal phases to prevent corrosion. One series of compounds applied to reduce copper and copper-alloy corrosion are aromatic organic corrosion inhibitors. This series of organic compounds, which includes mercaptobenzothiazole ("MBT"), benzotriazole ("BT"), butylbenzotriazole ("BBT"), tolytriazole ("TT"), naphthotriazole ("NTA") and related compounds, react with the metal surface and form protective films on copper and copper alloys. These compounds are active corrosion inhibition treatment components and are referred to generally herein as copper corrosion inhibitors or corrosion inhibitors, or as aromatic azoles, and at times as triazoles or aromatic (thio)(tri) azoles.

Active components may be lost due to deposit, corrosion, chemical and microbiological degradation processes and physical losses (blowdown, drift, incorrect feed rates, and the like) and combinations of such phenomena, which are discussed in more detail below. Monitoring the loss of an active treatment component, particularly if such monitoring permits the extent of loss to be quantified and if the monitoring is continuous, is an indicator of treatment program performance. Moreover, if such monitoring is continuous and the active component loss clearly determined, automatic control permits the corrosion inhibitor losses to be compensated for an dosage to be precisely controlled.

The conventional analytical procedure for analysis of copper corrosion inhibitors is a UV(ultraviolet light)-photolysis/photometric method, and is well known to persons of ordinary skill in the art. This method, however, has a number of limitations. It is not well suited for continuous monitoring and/or control. It provides results that are strongly dependent upon the operator's laboratory technique. It cannot distinguish the chemical structure of the aromatic azole that is present. Its observed response is non-linear with respect to aromatic azole dosage. It requires that the aromatic azole be degraded with an ultraviolet lamp in the presence of a color-forming reagent. The UV-photolysis/photometric method and its limitations are discussed in more detail below.

It is an object of the present invention to provide a method for monitoring and/or controlling copper corrosion inhibitor losses and/or dosages on a continuous basis. It is an object of the present invention to provide a method for monitoring and/or controlling copper corrosion inhibitor concentrations that is substantially independent of an operator's laboratory technique. It is an object of the present invention to provide a method for monitoring and/or controlling copper corrosion inhibitor concentrations that can distinguish the chemical structure of the aromatic azole that is present. It is an object of the present invention to provide a method for monitoring and/or controlling copper corrosion inhibitor concentrations that provides a response that is substantially linear to aromatic azole concentration. It is an object of the present invention to provide a method for monitoring and/or controlling copper corrosion inhibitor concentrations that does not require UV digestion of the aromatic azole. These and other objects of the present invention are described in more detail below.

DISCLOSURE OF THE INVENTION

The present invention provides a method for the monitoring and/or dosage control of corrosion inhibitors in aqueous systems comprising measuring the concentration of the corrosion inhibitor within the water system by fluorescence monitoring. In preferred embodiment the fluorescence monitoring is conducted on a continuous basis. In preferred embodiment, the method of the present invention is employed for on-line determination of corrosion inhibitors in aqueous systems, particularly in industrial cooling water streams. In further preferred embodiment, the fluorescence monitoring is employed to quantify the loss of the copper corrosion inhibitor, and to control the dosage thereof.

PREFERRED EMBODIMENTS OF THE INVENTION

A fluorescent compound may be characterized by its major fluorescence peaks, that is the excitation and emission wavelengths and fluorescence intensities for such major peaks. In Table 1 below there is given for several of the copper corrosion inhibitors a summary of such excitation/emission wavelengths that have been determined for use in the present invention. These wavelengths are listed below in nanometers ("nm"). In addition, Table 1 sets forth the relative fluorescence of each compound, at corrosion inhibitor actives concentrations of 2 parts per million by weight ("ppm") in water within the pH ranges specified, in comparison to 2-naphthalenesulfonic acid ("2-NSA"), at a 0.4 ppm actives concentration in water, measured at 277 nm (excitation)/334 nm (emission) at neutral pH, which is assigned the value of 1. The relative fluorescence values given were determined assuming that the excitation light intensity and efficiency of the fluorometer optics/detector are uniform at all specified wavelengths.

TABLE 1

| Corrosion Inhibitor | pH | Fluorescence Wavelengths Excitation (nm)/ Emission (nm) | Relative Fluorescence |
|---|---|---|---|
| Naphthotriazole | 4 to 11 | 363 nm/445 nm | 28 |
| Naphthotriazole | less than 0.5 | 363 nm/445 nm | 0.11 |
| Tolyltriazole | 4 to 8.5 | 285 nm/365 nm | 0.22 |
| Tolyltriazole | less than 0.5 | 280 nm/410 nm | 2.34 |
| Benzotriazole | 4 to 8.5 | 285 nm/365 nm | 0.1 |
| Benzotriazole | less than 0.5 | 280 nm/390 nm | 0.64 |
| Butylbenzotriazole | 4 to 8.5 | 285 nm/365 nm | 0.18 |
| Butylbenzotriazole | less than 0.5 | 280 nm/410 nm | 1.52 |

As seen from Table 1 above, the fluorescence of the triazoles may shift as pH is significantly reduced. For tolyltriazole, benzotriazole and butylbenzotriazole, for instance, the fluorescence intensities are constant over a pH range of from about 4 to about 9, but increase dramatically as the pH is lowered below 1, and the emission wavelength is red-shifted at acid pH. For naphthotriazole, the fluorescence intensities are constant over the pH range of from about 4 to about 11. In contrast to tolyltriazole, benzotriazole and butylbenzotriazole, however, the fluorescence intensities of naphthotriazole are dramatically reduced under acid conditions. The relative fluorencence values listed in Table 1 are a comparison of the aromatic azoles as 2 ppm solutions to 2-NSA as a 0.4 ppm solution at neutral pH because 2 ppm is a typical dosage for aromatic azoles in, for instance, cooling waters. Hence the relative fluorescence values listed in Table 1 above are comparisons between the fluorescence intensities of the active component aromatic azoles to the inert fluorescent tracer at the typical dosages of each.

pH also affects the background fluorescence. The effect of pH reduction on the background fluorescence of a number of cooling tower water samples from representative industries is shown in Table 2 below for such water samples at a neutral pH ("w/o acid") and after reduction of pH to less than 0.5 ("w/acid") in comparison to tolytriazole ("TT"). For such comparison, the fluorescence of a 2 ppm (as actives) TT solution is assigned the percentage of 100%, and the fluorescence of both the TT solution and the cooling water samples are measured at 285/365 nm (ex/em) for the "w/o acid" measurements and at 280/410 for the "w/acid" measurements. In all instances the background percent fluorescence in comparison to TT is dramatically reduced upon acidification for all cooling water samples tested. Such unexpected and dramatic reductions in background fluorescence intensities of many of the cooling water samples, together with the unexpected and dramatic increases in fluorescence intensities of most of the aromatic azoles, at low pH conditions, provide a dramatic enhancement to the monitoring and dosage control capabilities of the method of the present invention.

TABLE 2

Survey of Cooling Water System Tolyltriazole Background Fluorescence

| Cooling Water Sample No. | Percent TT Background Fluorescence | |
|---|---|---|
| | w/o acid | w/acid |
| 1 | 114% | 14.6% |
| 2 | 82% | 4.2% |
| 3 | 134% | 10.9% |
| 4 | 123% | 12.8% |
| 5 | 104% | 10.3% |
| 6 | 158% | 6.7% |
| 7 | 350% | 15.2% |

Moreover, it has been found that the inert 2-NSA tracer has a relative fluorescence at low pH, as measured against the 2 ppm (as actives) TT solution at low pH that was employed for the Table 1 data above, of far less than 0.1. This dramatic reduction in the relative fluorescence intensity of the inert tracer 2-NSA versus TT at acid pH eliminates any significant interference to TT fluorescence measurements. As to its percent TT background fluorescence, for instance, 2-NSA (again as a 0.4 ppm solution) has a relative percent TT background fluorescence of 54% w/o acid, which is reduced to 0% w/acid. Thus one can monitor the concentration of a aromatic azole such as TT, and thereby control its concentration, in the presence of an inert tracer such as 2-NSA without interference from such inert tracer.

The determination of the fluorescence characteristics of these corrosion inhibitors and the dependence of the fluorescence characteristics on pH of the aqueous environment in which the fluorescence is measured provides optimizations of the fluorimetric method of monitoring and controlling corrosion inhibitor dosage in aqueous systems. The fluorescence intensity dependence on pH exhibited by some aromatic azoles within the pH ranges of interest, particularly the surprising and significant increase in relative fluorescence intensity upon pH adjustment found for some aromatic azoles, enhances the ability of the present invention to monitor the level of the corrosion inhibitors, and by virtue of such precise monitoring, to control the dosage thereof. The choice of emission and excitation wavelengths also helps in selective monitoring of specific corrosion inhibitors. For NTA, for example, the choice of 363 nm for excitation and 445 nm for emission, together with its large sensitivity, helps in distinguishing it from the natural background fluorescence of the water or the fluorescence of an inert tracer when such compound is present. For TT, if monitoring at typical cooling water pH ranges is required, selecting an excitation/emission wavelength combination of 285 nm/350 nm would render the signals due to TT independent of pH.

This fluorimetric method can be described briefly as follows. A sample of water is taken from an aqueous system, and optionally its pH is adjusted. The fluorescence intensity of the sample at the desired emission wavelength, using the desired excitation wavelength, is measured with a SHADOWSCAN ™ or other fluorescence detector. (SHADOWSCAN is a trademark of Nalco Chemical Company.) The measured fluorescence intensity is then compared to a working curve drawn up using standards in the concentration range of interest and this comparison provides a precise determination of the concentration of the corrosion inhibitor in the water sample drawn from the system. This method can be conducted on a continuous basis, providing a continuous monitoring of changes in the concentration of the corrosion inhibitor in the aqueous system.

The UV-photolysis/photometric method for determining the concentration of aromatic azoles in an aqueous system is a spectrophotometry method which involves adding a spectrophotometric reagent to a water sample containing one or more aromatic azoles, and then irradiating the mixture with ultraviolet radiation for five minutes. The absorbance of the resulting yellow mixture is then measured at 425 nm. While this method is currently used in the industry, it has several significant disadvantages. The results of this method are extremely dependent on the time of exposure to UV radiation. Any deviation from the 5 minute exposure duration results in severe accuracy and precision problems. Other disadvantages include the method's poor sensitivity, its 10 minutes assay time, and the difficulties in using the method in continuous water streams, such as continuous cooling water streams. Further, the aromatic azoles are degraded during the irradiation, and hence an inherent drawback to this method is the impossibility of distinguishing one aromatic azole species from another. Moreover, most water samples obtained from cooling towers in the industry possess a natural yellow color. Therefore, distinguishing the color due to aromatic azole from the natural color of the water is difficult, especially given the low sensitivity of the UV-photolysis/photometric method.

The fluorimetric method of the present invention has the following advantages (described in more detail below) in comparison to the UV-photolysis/photometric method method:

1. The fluorescence method is simple to use, requiring no special reagents and little to no sample preparation.
2. The fluorescence method has a greater sensitivity, detecting aromatic azoles at concentrations of just a few ppb, while the UV-photolysis/photometric method has a detection limit of about 250 ppb when equal size sample containers are used.
3. The monitoring of aromatic azole by the fluorometric method is precise and accurate, irrespective of the nature of the aqueous system in which it is measured.
4. The fluorescence method has a greater precision, having a relative standard deviation of 0.2% versus 13% for the UV-photolysis/photometric method.
5. The fluorescence method has a very broad linear dynamic range which stretches through the useful range for applications such as cooling water.
6. The fluorescence method provides a means for continuous analysis versus 10 minutes for grab samples for the UV-photolysis/photometric method.
7. The fluorescence method provides measurement readings that are stable and do not deteriorate with time, while the yellow color of the samples prepared by UV-photolysis/photometric degrade with time.
8. The fluorescence method analysis can be performed without any interference from inert fluorescence tracers such as 2-NSA or vice versa.
9. The fluorescence method can distinguish between aromatic azole species.
10. The fluorescence method is suitable for continuous monitoring and dosage control.
11. The fluorescence method is not significantly dependent upon the operator's laboratory technique.
12. The fluorescence method does not require aromatic azole degradation.

For those applications of the present invention that do not encounter any significant interference from an inert tracer that is being already used in an industrial installation, the present fluorimetric method can be installed in the tracer system already being used for the inert tracer.

The method of the present invention may be used as a singular determination of the concentration of a given corrosion inhibitor, as intermittent monitoring, or as continuous monitoring, but since continuous monitoring is highly advantageous and difficult to achieve with standard methods, in preferred embodiment the present invention provides monitoring on a continuous or substantially continuous basis. The method of the present invention may be used for monitoring purposes alone, but since the precise monitoring provided by the present invention is most commonly desired to permit precise control over dosage, in preferred embodiment the present invention is a method for both such monitoring and such control.

The use of inert fluorescent tracers is a widely-used known practice in industrial aqueous systems such as cooling waters. The substituted polynuclear aromatic compounds are in a class comprised of numerous compounds, many of which differ from one another by the number and type of substitutents, and by the positions of the substituents on the naphthalene ring, and such differences affect a given compound's fluorescence characteristics. As shown in the Examples below, the present fluorimetric method requires the selection of an emission wavelength at which the corrosion inhibitor's fluorescence intensity is to be measured, which preferably is substantially free of interference from other fluorescent tracers and other species present in the water being monitored. Undesirable interference may be encountered when some other species has significant fluorescence emission about the emission wavelength selected for monitoring the given corrosion inhibitor. In certain of the Examples below, the existence of potential interference was investigated and overcome by the emission wavelength selection, which is a powerful benefit of florescence analysis method. Two alternative approaches for avoiding interferences from other fluorescent species in the aqueous system are to employ an inert tracer having fluorescence characteristics that do not interfere with the desired fluorimetric assay or to employ measurement conditions (such as acid pH) in which the fluorescence of the desired species is enhanced relative to the background fluorescence.

The use of such an inert fluorescent tracer in the aqueous system, and the monitoring of both such inert tracer and the active corrosion inhibitor by the fluorimetric method, is a preferred embodiment of the invention, and the benefits of both tracers may be realized.

The magnitude of a fluorescent signal, or relative fluorescence, is the product of its fluorescent quantum yield multiplied by its light absorbance molar extinction coefficient and the concentration of the fluorescent species. The feasibility of detecting any fluorescent compound by a fluorimetric method is related to the fluorescence of the analyte (for each combination of excitation/emission wavelengths) versus the fluorescent background of the environment in which the fluorescent analyte will be measured. The aromatic azoles are inherently significantly fluorescent, and they are active corrosion inhibitors or corrosion inhibitor components. The present invention has determined a means of employing such inherent fluorescent characteristics to directly monitor, and provide precise dosage control of, such active corrosion inhibitor species. Moreover the present method has been found to be extremely precise and advantageous for determining precisely the concentrations of such active corrosion inhibitors by avoiding and minimizing the fluorescence background of aqueous systems such as cooling waters, and at the concentrations of the active corrosion inhibitors normally encountered in cooling waters down to much lower levels. The present invention is also advantageous because the active corrosion inhibitors are being directly monitored, without chemical degradation.

As noted above, the copper corrosion inhibitors for which the fluorimetric method is applicable are, as a class, generally compounds containing the heterocyclic five-membered triazole ring structure (in unsubstituted form having the formula of $C_2H_3N_3$) and an aromatic substituent to such ring structure, which aromatic substituents include tolyl, benzo, naphtho, and like aromatic substituent(s), which may be further substituted, for instance with alkyl substituent(s) having from about 1 to about 10 carbons, or halides, hydroxyls, alkenes, alkynes, sulfonates, carboxylates, amines, amides, and the like. By substituent is meant herein a radical other than hydrogen. Moreover, the substituent(s) and/or combinations of substituents to the aromatic substituent of a copper corrosion inhibitor may be any substituent within such broad definition of "other than hydrogen" provided that such substituent(s) and/or combination of substituents do not bring the compound in question outside of the corrosion inhibitor category. Not all of the copper corrosion inhibitors, however, are triazoles. Mercaptobenzothiazole ($C_7H_5NS_2$), while formed in part of a heterocyclic ring and in part by an aromatic ring, is not a triazole, and yet has like properties as to corrosion inhibition and fluorescence. Hence while the terms "azoles" or at times "triazoles" might be used herein for the entire class of compounds, as done also in the field, the more apt term for this class is "aromatic azole(s)".

EXAMPLE 1

Figure 1:
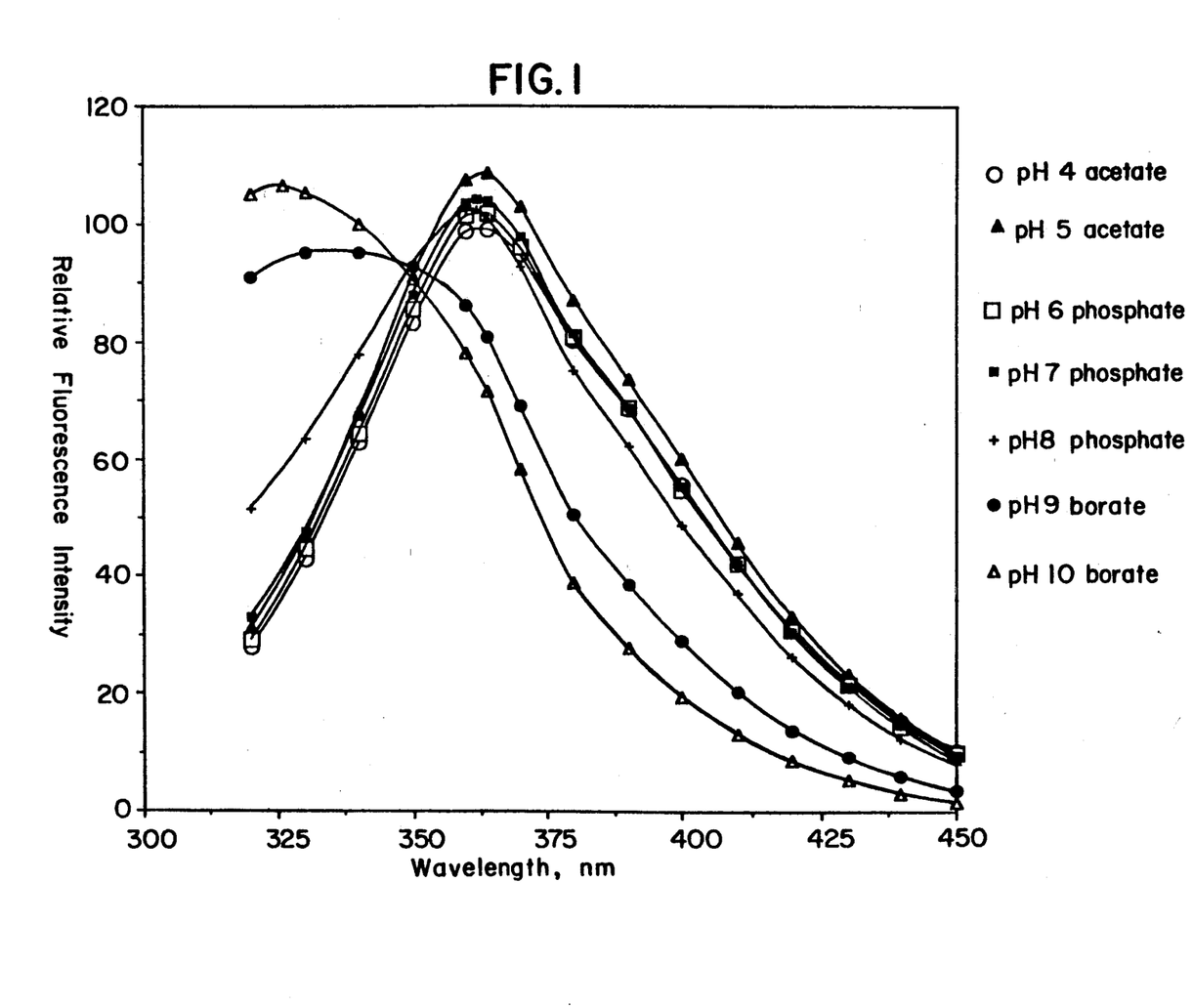
FIG. 1 is a fluorescence spectra of tolyltriazole showing an isoemission point.

In Example 1, a fluorescence based method was used to determine quantitatively the concentration of tolyltriazole ("TT") by a method that could be used in the presence of other fluorescent species, such as an inert fluorescent tracer. As a preliminary matter, the fluorescence spectra of TT versus specific pH ranges of TT aqueous solutions were determined as follows. 2 ppm TT aqueous solutions were prepared in 10 mM buffer solutions in the pH range between 10 and 1.3. Borate buffers were used for solutions in the pH 8.5 to 10 range. Phosphate buffers were used for solutions in the pH 6 to 8.5 range. Acetate buffers were used for solutions in the pH 4 to 5 range. Citrate buffers were used for solutions in the pH 1 to 3 range. Using an excitation wavelength of 285 nm, the fluorescence spectra for these samples were obtained and are shown in FIG. 1, except for samples below a pH of 4. As the pH decreased below a pH of 4, the fluorescence intensities of the samples became stronger as the pH decreased, and the original calibration of the plot was no longer applicable. As seen in FIG. 1, an isoemission point, which is independent of pH, exists at about 350 nm. In the pH range of from 4 to 8.5, the peak position, as well as the fluorescence intensities, remain substantially constant. Below pH 3 (not shown in FIG. 1), a new peak centered around 412 nm appeared, in addition to the 365 nm peak, and as the pH decreased further, the peak at 412 nm (due to cationic, protonated TT) increased further while the peak at 365 nm (due to neutral TT) decreased until the fluorescence of TT was represented by a single peak centered around 412 nm at the pH of 1.31. In this Example 1, standard solutions were prepared containing TT concentrations from 5 parts per billion by weight ("ppb") to 2 ppm. 3 ml of each of these solutions was pipetted into a cuvette and 0.075 ml of 50% $H_2SO_4$ was added. The fluorescence intensity at an excitation wavelength of 280 nm and an emission wavelength of 410 nm was determined. The fluorescence of each of those solutions was plotted and a linear working curve (shown in FIG. 2) was obtained. The detection limit was found to be 0.005 ppm. This working curve was used to obtain the concentration of TT in a cooling water sample known to contain TT. The result obtained was 0.49 ppm of TT, compared to a concentration of 0.52 ppm TT determined by HPLC (high pressure liquid chromatography).

EXAMPLE 2

To determine the extent of interferences, if any, from substances commonly added to cooling water streams, sixty formulations were reviewed and representative samples of cooling water formulations which contain other fluorescent substances were tested to determine the dosage required for 10 percent interference with the fluorimetric method for monitoring aomatic azoles, in the acid (less than 0.5 pH) domain. For these determinations, each formulation was diluted with water to its typical use (dosage) concentration, and the fluorescence of diluted formulations were measured (280 nm excitation/410 nm emission wavelengths). The fluorescence spectra were compared to that of aqueous solutions containing 2 ppm TT, and the dosage of the formulation required to see a 10% interference of the TT spectra was determined, assuming a proportional increase in fluorescence intensity with dosage increase. The 2 ppm solution of TT was assigned a value of 100% at 280 nm/390 nm, for the determination of 10% interference dosage for assays of TT, which are set forth below in Table 3, together with the typical dosages thereof, and the types of substance in terms of use characteristics.

TABLE 3

| Formulation Designation | Substance Type | Typical Product Dosage | Dosage Req. for 10% Interference |
| --- | --- | --- | --- |
| a | Anti-microbial | 50–150 ppm | 1660 ppm |
| b | Corrosion Inhibitor | 50 ppm | 480 ppm |
| c | Dispersant | 40 ppm per ppm of iron | >1000 ppm |
| d | Corrosion/scale Inhibitor | 1000 ppm | 785 ppm |
| e | Iron Dispersant | 10–30 ppm | 1464 ppm |
| f | Oil Dispersant | 10–30 ppm | 636 ppm |
| g | Antimicrobial | 200 ppm | 202 ppm |
| i | Corrosion Inhibitor | 50–100 ppm | >1000 ppm |
| j | Dispersant | 35 ppm | >1000 ppm |

EXAMPLE 3

Figure 2:
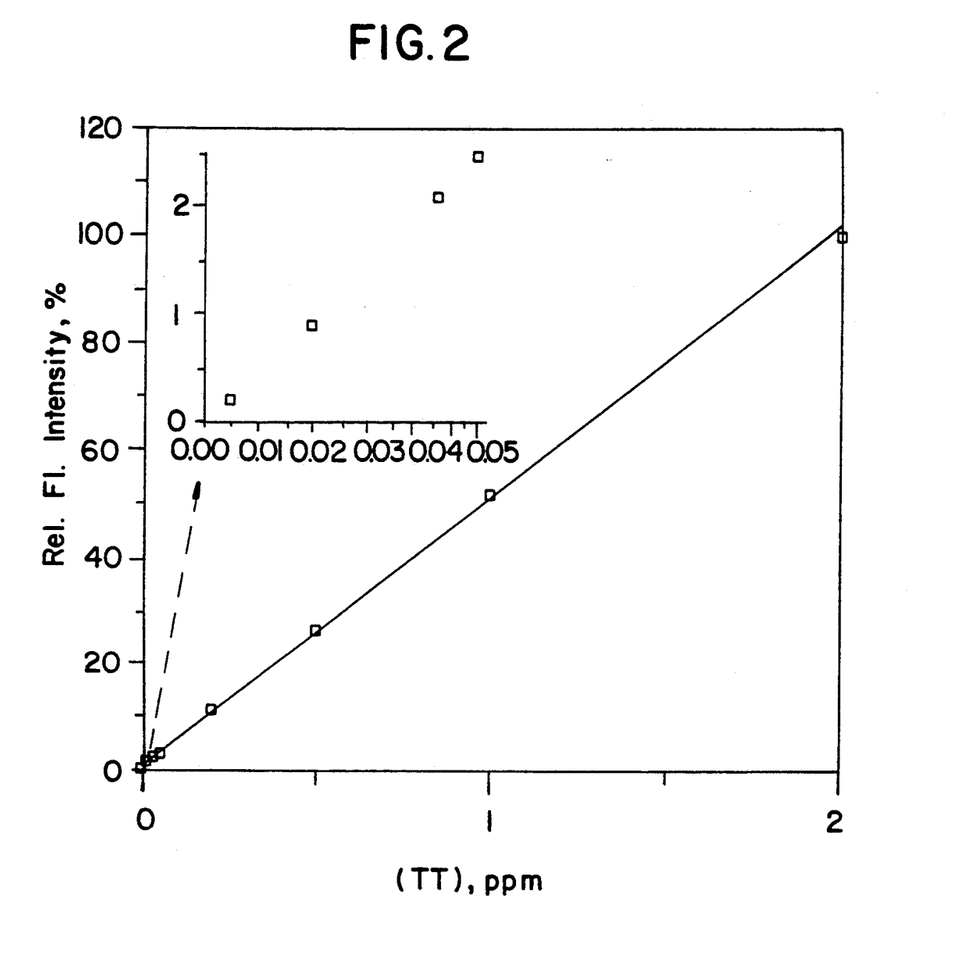
FIG. 2 is a working curve for tolytriazole showing fluorescence intensity versus tolytriazole concentration in aqueous solutions, down to a tolytriazole concentration of 5 parts per billion (ppb).
Figure 3:
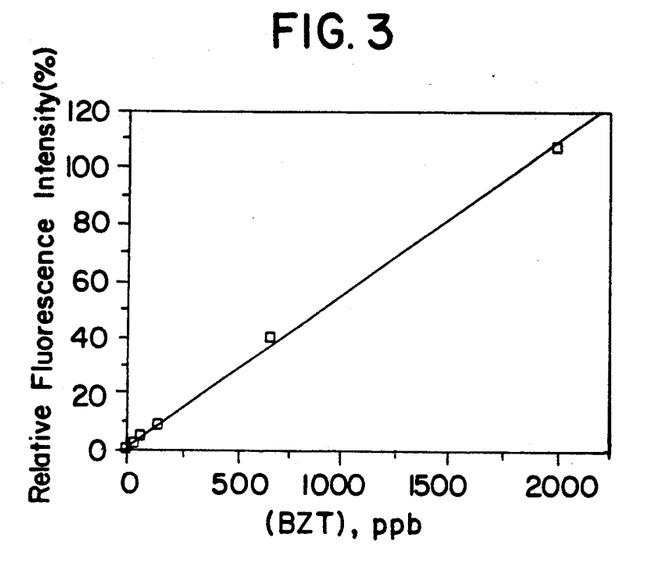
FIG. 3 is a working curve for benzotriazole showing fluorescence intensity versus benzotriazole concentration in aqueous solutions.
Figure 4:
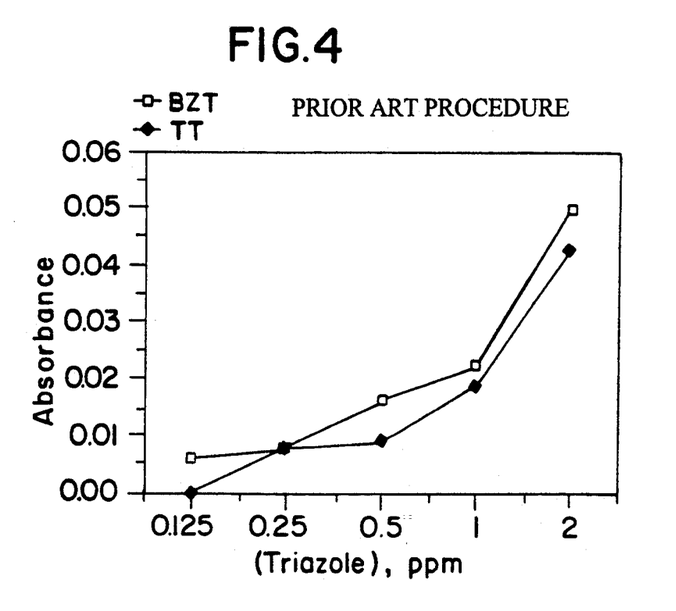
FIG. 4 is a UV-photolysis/photometric method plot of working curves for tolytriazole and benzotriazole.

Using aqueous solutions of BT at concentrations down to very low concentrations of BT actives, the fluorescence intensities were measured at 390 nm (excitation wavelength of 280 nm), and the intensities versus concentrations of BT, in ppb, were plotted to provide a working curve for BT, shown in FIG. 3. In comparison, FIG. 4 shows the working curves for both BT and TT provided by the UV-photolysis/photometric method, both of which are nonlinear. The detection limits for BT and TT provided by the UV-photolysis/photometric method working curves shown in FIG. 4 are both down to about 125 ppb (0.125 ppm), but are very flat for concentrations lower than 0.5 ppm. Moreover most industrial cooling waters have a natural absorbance at 425 nm. Therefore, precise analysis at low concentrations is extremely difficult. In comparison, the fluorimetric method working curve for BT (FIG. 3) is linear down to about 33 ppb, and as noted above the working curve for TT by the fluorimetric method is linear down to a concentration of about 5 ppb (as shown in FIG. 2). For a 2 ppm concentration of triazole, the % relative standard deviation for the fluorimetric method was 0.2% (with an 8 s integration time constant and 3 replicate measurements), while the % relative standard deviation by the UV-photolysis/photometric method was about 13%.

EXAMPLE 4

Figure 5:
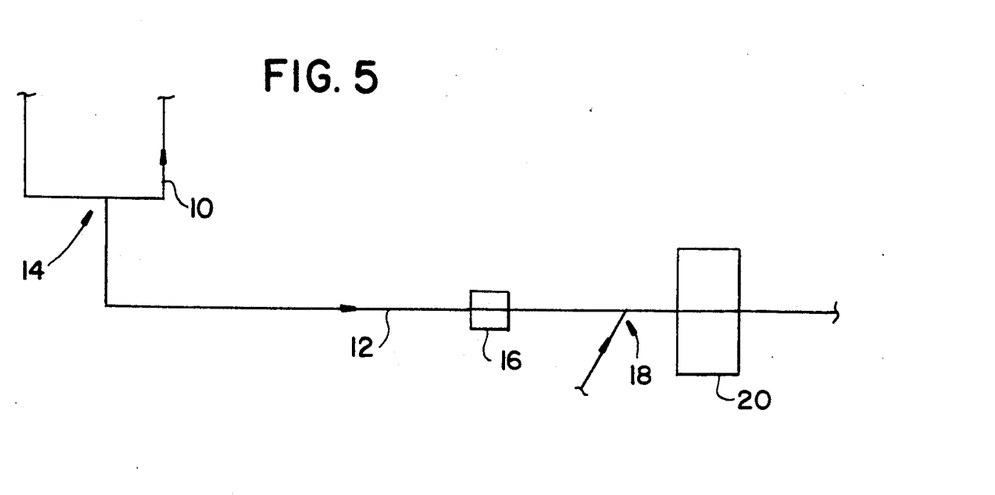
FIG. 5 is a schematic drawing of an intermittent or continuous mode of the present invention.
Figure 6:
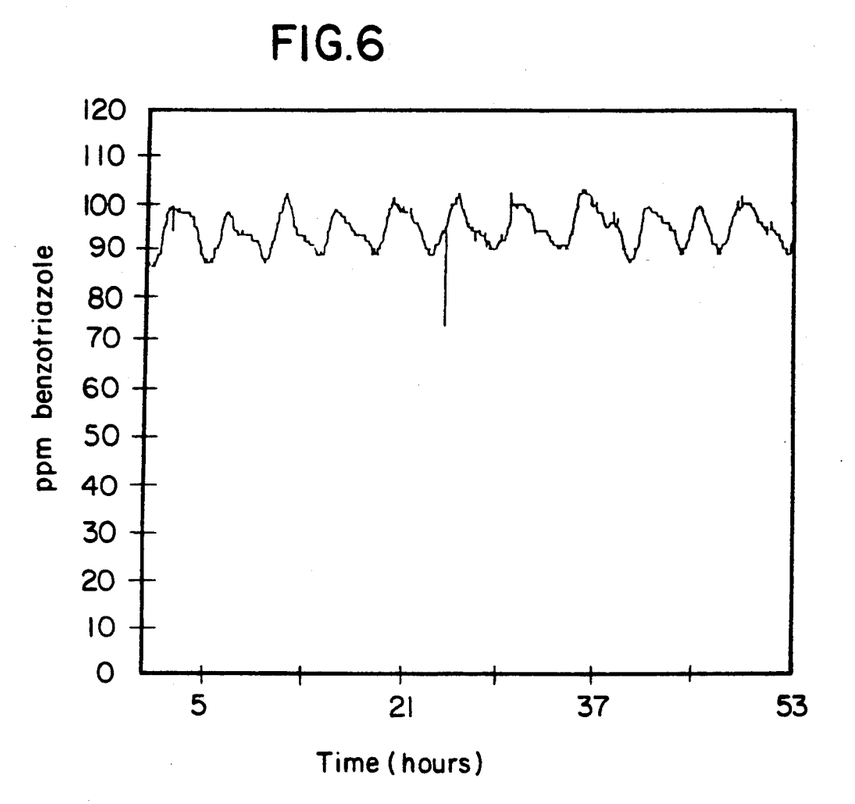
FIG. 6 is a plot of a continuous monitoring of benzotriazole concentration in a pilot cooling tower evaluation of a cooling water treatment program.

Continuous monitoring/control of BT concentrations was conducted in a Pilot Cooling Tower using a commercial (Nalco Chemical Company) BT-containing water treatment formulation. FIG. 5, which is described in more detail below, shows the general continuous sampling technique used. A target feed rate of 1 ppm BT actives was chosen. Grab samples of the cooling water were taken from the Pilot Cooling Tower and assayed for BT using HPLC, and then those results were compared to the setpoint of 1 ppm BT. The results from this continuous monitoring/control of BT concentration are shown in FIG. 6. It can be seen from these results that BT levels were controlled at 1 ppm±0.05 ppm.

EXAMPLE 5

The pH dependence of a 2,3-naphthotriazole ("2,3-NTA") fluorescent tracer, within the pH range of from 3.5 to 11.5 was determined. 2,3-NTA was found to have excitation maxima at 328 nm, 363 nm, and 378 nm, and emission maxima at 385 nm, 407 nm, and 424 nm. An isoemissive point (which provides a constant fluorescence over the pH range of 4 to 11) was identified at 363 nm/445 nm. At these pH values, the relative fluorescence intensity of a solution containing 2 ppm of 2,3-NTA (typical usage concentration) was determined to be 28 times that of a solution containing 0.4 ppm of 2-NSA (excitation at 277 nm and emission at 334 nm). At highly acidic pH, the fluorescence of 2,3-NTA and 2-NSA are unexpectedly and significantly reduced due to reversible protonation of sulfonic acid and triazole ring, respectively. The reduced fluorescence of 2,3-NTA was particularly because the other aromatic azoles (TT, BT and BBT) showed significantly increased fluorescence at very acidic pH values.

EXAMPLE 6

Figure 7:
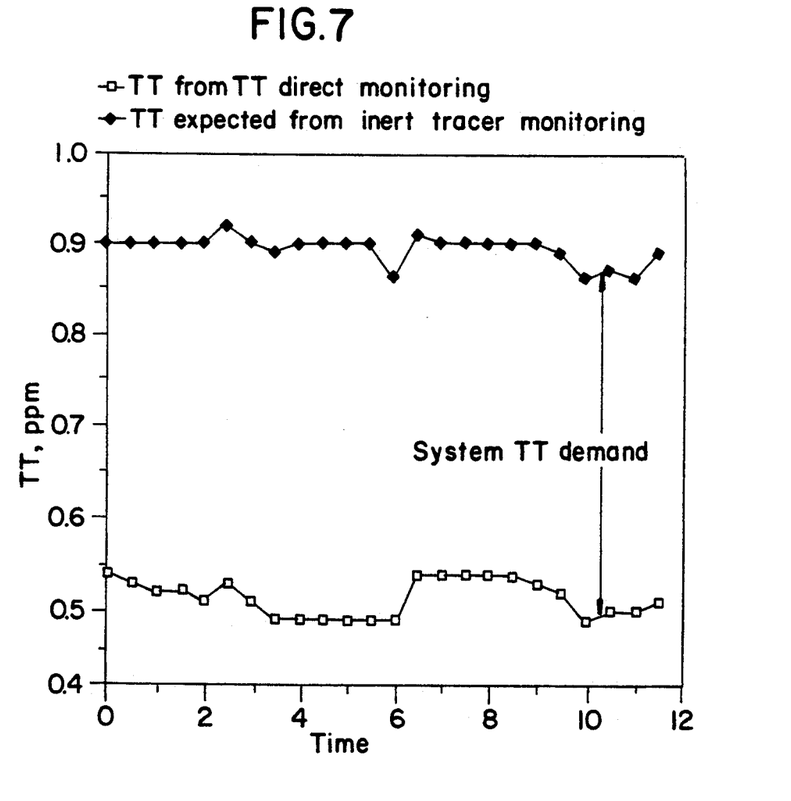
FIG. 7 is a plot of a continuous monitoring of tolytriazole and an inert tracer as a measure of cooling system demand (uptake) of tolytriazole.

An industrial cooling water system containing an open recirculating cooling tower was fed TT based on inert fluorescent tracer levels. The target TT concentration was 0.9 ppm in the recirculating system. The TT concentration was also monitored directly at 280 nm/410 nm using a 10% sulfuric acid solution to enhance TT signals and to suppress background. The difference between the results expected from the inert tracer readings and direct TT monitoring constitutes system demand. The results are shown in FIG. 7. It can be clearly seen that the system exhibits a large demand for TT.

The water samples identified in the Examples above as cooling water were obtained from pilot cooling towers that simulate industrial cooling towers as to substances in the cooling waters (substances normally encountered in the feed water and substances added thereto for various purposes) and environmental conditions, such as temperature and the like, and representative industrial cooling water systems.

A survey of potential interferences from other cooling water products shown in Example 2 above indicates that for most such products a 10% interference would require such products to be present in concentrations of about 10 or 100 or more times the normal dosage concentration, and hence no interference of any significance was determined with respect to TT or BT.

In addition to the survey of potential interference from cooling water additives, the effect of $Cu^{+2}$ ions (such as would occur from corrosion of copper alloys) on the fluorescence levels of the triazoles was investigated and determined to be substantially nonexistent.

When a given aromatic azole can be assayed without a fluorescence intensity dependency in a pH range of from about a pH of 4 to about a pH of 9, such as tolyltriazole, the determination may be conducted in such neutral pH domain. The water of many aqueous systems, including cooling waters, is routinely within a neutral pH range (7 to 9), and hence it is possible in fluorimetric method assay to require no pH adjustment. This is particularly true for aromatic azoles with very high relative fluorescence (e.g., 2,3-naphthotriazole). When a given aromatic azole has a higher relative intensity in an acid pH domain, such as a pH of less than 0.5, for instance tolyltriazole, benzotriazole and butylbenzotriazole, and a high background fluorescence exists near neutral pH, the additional step of adjusting the pH may in many instances be beneficial by almost completely eliminating that background fluorescence interference. The elimination of interferences is due not only to the greater relative fluorescence of such aromatic azoles under acid conditions but also the reduction of the relative fluorescence of most other molecules, including 2-NSA, by such acid conditions. The use of an acid domain was found to provide an accurate assay for TT at a concentration level of 0.52 ppm in a commercially-derived water sample with a large fluorescence background, of unknown nature, that assay by the fluorimetric method under neutral pH conditions was not possible.

While the procedures described in some of the above Examples were performed as assays for batch samples, as noted elsewhere herein the method in preferred embodiment is used on a continuous basis. One preferred mode for an industrial intermittent or continuous method, as shown in FIG. 5, would be to provide a sidestream 12 to, for instance, a cooling water loop 10, through which small volumes of the water from the aqueous system would be intermittently or continuously flow. Downstream from the sidestream inlet 14 should preferably be a filter 16 to remove solids before the assay point. Along the sidestream 12 there optionally may be an interconnecting charge point 18 for the addition of substances to the water, such as acid, when an acid domain assay is desired, and/or other materials, such as may be deemed appropriate. Downstream of such addition point 18 would be the assay point 20 equipped with a SHADOWSCAN ™ fluorescence detector (SHADOWSCAN is a trademark of Nalco Chemical Company) with appropriate filters, or other fluorescence detector, set to fluoresce the aromatic azole and measure the fluorescence intensity at the selected wavelengths.

Sulfuric acid is the acid of choice for acidification of water samples prior to assay, and the final acid concentration of such samples preferably is greater than 3 weight percent.

In one embodiment, the present invention is a method for monitoring the concentration of a aromatic azole corrosion inhibitor in the water of an aqueous system, comprising fluorescing a sample of the water from the aqueous system, measuring the fluorescence intensity of the sample, and comparing such fluorescence intensity to a curve from a plot of known concentrations of the aromatic azole in aqueous solutions versus the fluorescence intensities of such solutions, wherein the fluorescence excitation/emission wavelengths and the pH domain the plot and the sample solutions are the same, whereby the concentration of the aromatic azole is determined by correspondence to its fluorescence intensity. In preferred embodiment, such method further includes the step of adjusting the pH of the sample prior to the fluorescing of the sample, particularly wherein the pH is adjusted by the addition of sulfuric acid so as to obtain a final acid concentration of 3 wt. percent (a pH of less than 0.5), although more broadly speaking adjusting the pH to a value of less than 1.5 is also a preferred embodiment. In preferred embodiment, the aromatic azole is present in the water in the amount of from about 1 part per billion by weight to about 1000 parts per million by weight. In further preferred embodiment, the water has a pH within the range of from about 4 to about 9, and the fluorescing is conducted at excitation/emission wavelengths of about 285/350 nm, and for such embodiment the emission wavelength may an isoemissive wavelength rather than a fluorescence peak. In other preferred embodiments the aromatic azole is tolyltriazole or butylbenzotriazole, the water has a pH of less than about a pH of 1.5, and more preferably a pH of less than about 0.5, and the fluorescing is conducted at excitation/emission wavelengths of about 280/410 nm; the aromatic azole is benzotriazole, the water has a pH of less than about 1.5, and more preferably less than about 0.5, and the fluorescing is conducted at excitation/emission wavelengths of about 280/390 nm; and, the aromatic azole is naphthotriazole, the water has a pH within the range of from about 4 to about 11, and the fluorescing is conducted at excitation/emission wavelengths of about 363/445 nm. In another preferred embodiment of the invention, the fluorescing, the comparing and the determination of aromatic azole concentration are conducted on a continuous basis. In further preferred embodiment, the aqueous system is an industrial aqueous system, such as a steam-generating system (boiler), a cooling water system, a manufacturing process water system, and the like.

The present invention is also a method for controlling the concentration of a aromatic azole corrosion inhibitor in the water of an aqueous system, comprising fluorescing a sample of the water from the aqueous system, measuring the fluorescence intensity of the sample, comparing such fluorescence intensity to a curve from a plot of known concentrations of the aromatic azole in aqueous solutions versus the fluorescence intensities of such solutions, wherein the fluorescence excitation/emission wavelengths and the pH domain, the plot and the sample solutions are the same, whereby the concentration of the aromatic azole is determined by correspondence to its fluorescence intensity, and adding to the aqueous system a sufficient amount of the aromatic azole to provide the desired total concentration of the aromatic azole in the aqueous system. All of the preferred embodiments set forth above for the method of monitoring a aromatic azole corrosion inhibitor in an aqueous system are also preferred embodiments to the method of controlling the concentration of a aromatic azole corrosion inhibitor in an aqueous system.

The present invention is also such methods of monitoring the concentration of an aromatic azole and of controlling the concentration of such aromatic azole, further wherein the water and the sample of the water contain an inert fluorescent tracer, the measuring of the fluorescence intensity of the sample also includes the measuring of the contribution to the fluorescence intensity from the inert tracer, the aromatic azole concentration based on the contribution to the fluorescence intensity from the inert tracer is also determine and the system demand for the aromatic azole is determined from the difference between the aromatic azole concentration based on the contribution to the flourescence intensity from the inert tracer and the aromatic azole concentration based its the fluorescence intensity. This preferred embodiment is particularly demonstrated in Example 6 above.

As the selection of a suitable excitation/emission wavelength combination, preferably the emission wavelength is a wavelength centered at one of the corrosion inhibitor's strongest peaks, when the corrosion inhibitor is in a pH domain in which its fluorescence spectra is independent of pH. Such a major peak choice is particularly preferred when there is little to no fluorescence interference at such wavelength from substances that may be present in the water sample. Another preferred selection is an emission wavelength that corresponds to an isoemission point of the corrosion inhibitor, when the corrosion inhibitor is in a pH domain in which its fluorescence spectra is independent of pH. Such a isoemission point choice is particularly preferred when there is little to no fluorescence interference at such isoemission point.

When concentrations are expressed herein in parts per million ("ppm") or parts per billion ("ppb"), the parts are always parts by weight per million or billion parts by volume, wherein the weight/volume units are equivalent to grams/milliliters. Such concentrations generally a close approximation to a weight/weight basis, such as parts by weight per million parts by weight for "ppm", but the weight/volume basis is nonetheless more accurate.

Wavelengths as stated herein are always in nanometers ("nm"), and when a set of wavelengths are set forth separated by a slash ("/") herein, the first wavelength is the fluorescence excitation wavelength and the second is the fluorescence emission wavelength.

INDUSTRIAL APPLICABILITY OF THE INVENTION

The present invention is applicable to industries that require corrosion inhibitors for aqueous systems, such as cooling water systems, boilers, and other water streams, and in particular for industrial scale aqueous systems.

We claim:

1. A method for controlling the concentration of an aromatic azole corrosion inhibitor in the water of an industrial aqueous system, comprising:
    fluorescing a sample of said water from said aqueous system;
    measuring the fluorescence intensity of said sample;
    comparing said fluorescence intensity to a curve from a plot of known concentrations of said aromatic azole in aqueous solutions versus the fluorescence intensities of said solutions,
    wherein the fluorescence excitation/emission wavelengths and the pH domain of said plot and said sample are comparable,
    whereby the concentration of said aromatic azole is determined by correlation to its fluorescence intensity;
    wherein said measuring is conducted on a substantially continuous basis; and
    adding to said aqueous system a sufficient amount of said aromatic azole to provide a desired total concentration of said aromatic azole in said aqueous system.

2. The method of claim 1 further including the step of adjusting the pH of said sample prior to said fluorescing of said sample,
    wherein said pH is adjusted by the addition of a mineral acid to a pH of less than 1.5.

3. The method of claim 1 wherein said water has a pH within the range of from about 4 to about 9, and said fluorescing is conducted at excitation/emission wavelengths of about 285/350 nm.

4. The method of claim 1 wherein said aromatic azole is tolyltriazole or butylbenzotriazole, said water has a pH of less than about a pH of 1.5, and said fluorescing is conducted at excitation/emission wavelengths of about 280/410 nm.

5. The method of claim 1 wherein said aromatic azole is benzotriazole, said water has a pH of less than about 1.5, and said fluorescing is conducted at excitation/emission wavelengths of about 280/390 nm.

6. The method of claim 1 wherein said aromatic azole is naphthotriazole, said water has a pH within the range of from about 4 to about 11, and said fluorescing is conducted at excitation/emission wavelengths of about 363/445 nm.

7. The method of claim 1 further wherein;
    said water and said sample of said water contain an inert fluorescent tracer;
    said measuring of the fluorescence intensity of said sample also includes the measuring of the contribution to said fluorescence intensity from said inert tracer;
    the aromatic azole concentration based on the contribution to said fluorescence intensity from said inert tracer is also determined; and
    the system demand for said aromatic azole is determined from the difference between the aromatic azole concentration based on the contribution to said fluorescence intensity from said inert tracer and said aromatic azole concentration based its said fluorescence intensity.

8. A method for monitoring the concentration of an aromatic azole corrosion inhibitor in the water of an industrial aqueous system, comprising:
    fluorescing a sample of said water from said aqueous system;
    measuring the fluorescence intensity of said sample; and
    comparing said fluorescence intensity to a curve from a plot of known concentrations of said aromatic azole in aqueous solutions versus the fluorescence intensities of said solutions,
    wherein the fluorescence excitation/emission wavelengths and the pH domain of said plot and said sample are comparable, and
    whereby the concentration of said aromatic azole is determined by correlation to its fluorescence intensity.

9. The method of claim 8 further including the step of adjusting the pH of said sample by the addition of a mineral acid to a pH of less than 1.5 prior to said fluorescing of said sample.

10. The method of claim 8 wherein said water has a pH within the range of from about 4 to about 9, and said fluorescing is conducted at excitation/emission wavelengths of about 285/350 nm.

11. The method of claim 8 wherein said aromatic azole is tolyltriazole or butylbenzotriazole, said water has a pH of less than about a pH of 1.5, and said fluorescing is conducted at excitation/emission wavelengths of about 280/410 nm.

12. The method of claim 8 wherein said aromatic azole is benzotriazole, said water has a pH of less than about 1.5, and said fluorescing is conducted at excitation/emission wavelengths of about 280/390 nm.

13. The method of claim 8 wherein said aromatic azole is naphthotriazole, said water has a pH within the range of from about 4 to about 11, and said fluorescing is conducted at excitation/emission wavelengths of about 363/445 nm.

14. The method of claim 8 wherein said fluorescing, said comparing and said determination of aromatic azole concentration are conducted on a continuous basis.

15. The method of claim 8 wherein said industrial aqueous system is an industrial steam-generating water system, a cooling water system or a manufacturing process water system.

16. The method of claim 8 further wherein;
    said water and said sample of said water contain an inert fluorescent tracer;

said measuring of the fluorescence intensity of said sample also includes the measuring of the contribution to said fluorescence intensity from said inert tracer;

the aromatic azole concentration based on the contribution to said fluorescence intensity from said inert tracer is also determined; and the system demand for said aromatic azole is determined from the difference between the aromatic azole concentration based on the contribution to said fluorescence intensity from said inert tracer and said aromatic azole concentration based on its said fluorescence intensity.

17. A method for monitoring the concentration of an aromatic azole corrosion inhibitor in the water of an industrial aqueous system, comprising:

sampling the water of an industrial aqueous system by isolating a sample of said water from said aqueous system;

fluorescing said sample;

measuring the fluorescence intensity of said sample; and comparing said fluorescence intensity to a curve from a plot of known concentrations of said aromatic azole in aqueous solutions versus the fluorescence intensities of said solutions, wherein the fluorescence excitation/emission wavelengths and the pH domain of said plot and said sample are comparable, and whereby the concentration of said aromatic azole is determined by correlation to its fluorescence intensity, wherein said sampling, said fluorescing and said concentration determination are conducted on a substantially continuous basis.

18. The method of claim 17 wherein said sample is adjusted by the addition of a mineral acid to a pH of less than about 1.5 prior to said fluorescing, and said aromatic azole is tolyltriazole, butylbenzotriazole or benzotriazole.

19. A method for monitoring the concentration of an aromatic azole corrosion inhibitor in the water of an aqueous system, comprising:

fluorescing a sample of said water from said aqueous system;

measuring the fluorescence intensity of said sample; and comparing said fluorescence intensity to a curve from a plot of known concentrations of said aromatic azole in aqueous solutions versus the fluorescence intensities of said solutions, wherein the fluorescence excitation/emission wavelengths and the pH domain of said plot and said sample are comparable, whereby the concentration of said aromatic azole is determined by correlation to its fluorescence intensity, and further wherein:

said water and said sample of said water contain an inert fluorescent tracer;

said measuring of the fluorescence intensity of said sample also includes the measuring of the contribution to said fluorescence intensity from said inert tracer;

the aromatic azole concentration based on the contribution to said fluorescence intensity from said inert tracer is also determined; and the system demand for said aromatic azole is determined from the difference between the aromatic azole concentration based on the contribution to said fluorescence intensity from said inert tracer and said aromatic azole concentration based on its said fluorescence intensity.

20. A method for monitoring the concentration of an aromatic azole corrosion inhibitor in the water of an aqueous system, comprising:

fluorescing a sample of said water from said aqueous system;

measuring the fluorescence intensity of said sample; and comparing said fluorescence intensity to a curve from a plot of known concentrations of said aromatic azole in aqueous solutions versus the fluorescence intensities of said solutions, wherein the fluorescence excitation/emission wavelengths and the pH domain of said plot and said sample are comparable, wherein the concentration of said aromatic azole is determined by correlation to its fluorescence intensity, and further wherein said sample is adjusted by the addition of a mineral acid to a pH of less than about 1.5 prior to said fluorescing.

21. The method of claim 20 wherein said aromatic azole is tolyltriazole, butylbenzotriazole or benzotriazole.

22. The method of claim 20 wherein said monitoring is conducted on a substantially on-line continuous basis.

* * * * *

UNITED STATES PATENT AND TRADEMARK OFFICE
CERTIFICATE OF CORRECTION

PATENT NO. : 5,278,074
DATED : January 11, 1994
INVENTOR(S) : Narasimha M. Rao, et al It is certified that error appears in the above-indentified patent and that said Letters Patent is hereby corrected as shown below:

IN THE DRAWINGS, SHEET 5, FIG. 6, THE Y AXIS

SHOULD READ AS FOLLOWS:

1.20
1.10
1.00
 .90
 .80
 .70
 .60
 .50
 .40
 .30
 .20
 .10
  0

Signed and Sealed this

Seventeenth Day of October, 1995

Attest:

BRUCE LEHMAN

*Attesting Officer*        *Commissioner of Patents and Trademarks*